US011971398B2

(12) United States Patent
Hill et al.

(10) Patent No.: US 11,971,398 B2
(45) Date of Patent: Apr. 30, 2024

(54) METHODS FOR DETECTION OF LEAD IN WATER

(71) Applicant: NanoSafe, Inc., Blacksburg, VA (US)

(72) Inventors: William Cary Hill, Blacksburg, VA (US); Matthew Scott Hull, Dublin, VA (US)

(73) Assignee: ITA International, LLC, Newport News, VA (US)

( * ) Notice: Subject to any disclaimer, the term of this patent is extended or adjusted under 35 U.S.C. 154(b) by 107 days.

(21) Appl. No.: 16/543,069

(22) Filed: Aug. 16, 2019

(65) Prior Publication Data

US 2020/0057042 A1    Feb. 20, 2020

Related U.S. Application Data

(60) Provisional application No. 62/719,454, filed on Aug. 17, 2018.

(51) Int. Cl.
*G01N 21/82*    (2006.01)
*G01N 31/02*    (2006.01)
(Continued)

(52) U.S. Cl.
CPC ......... *G01N 33/1813* (2013.01); *G01N 31/22* (2013.01); *G01N 33/182* (2013.01);
(Continued)

(58) Field of Classification Search
CPC .... G01N 21/82; G01N 31/02; G01N 33/1813; G01N 33/182; G01N 31/22; G01N 21/293; G01N 21/78; G01N 33/18
(Continued)

(56) References Cited

U.S. PATENT DOCUMENTS 3,806,319 A    4/1974    Fabbro et al.
3,809,537 A    5/1974    Horine
(Continued)

FOREIGN PATENT DOCUMENTS

CA    2026362 A1 *    12/1991
CA    2026362 A1    12/1991
(Continued)

OTHER PUBLICATIONS

Kopittke, P.M. et al. "Toxic effects of Pb2+ on the growth and mineral nutrition of signal grass (*Brachiaria decumbens*) and Rhodes grass (*Chloris gayana*)," Plant Soil (2007) 300: 127-136. (Year: 2007).*

(Continued)

*Primary Examiner* — Jennifer Wecker
*Assistant Examiner* — Michelle Adams
(74) *Attorney, Agent, or Firm* — New River Valley IP Law, P.C.; Michele L. Mayberry; Ashley M. Gates

(57) ABSTRACT

Methods, apparatuses, and kits for detection of substances in water by forming a complex with an indicator reagent and filtering the complex on a filter or membrane are described. The concentrated indicator on the filter, membrane or other capture device provides a colorimetric readout that can determine the amount of substance present in a water sample. A computer-implemented method for determining the concentration of substances in water based on color data from the colorimetric readout is also described.

6 Claims, 6 Drawing Sheets

(51) Int. Cl.
*G01N 31/22* (2006.01)
*G01N 33/18* (2006.01)
*G01N 21/78* (2006.01)

(52) U.S. Cl.
CPC ............. *G01N 21/78* (2013.01); *G01N 21/82* (2013.01); *G01N 31/02* (2013.01)

(58) Field of Classification Search
USPC .......................................................... 436/73
See application file for complete search history.

(56) References Cited

U.S. PATENT DOCUMENTS

| | | | |
|---|---|---|---|
| 3,967,932 | A | 7/1976 | Sano et al. |
| 4,777,143 | A | 10/1988 | Price et al. |
| 4,829,007 | A | 5/1989 | Koslow |
| 4,873,197 | A | 10/1989 | Gould |
| 5,010,020 | A | 4/1991 | Gould |
| 5,019,516 | A | 5/1991 | Wiese |
| 5,039,618 | A | 8/1991 | Stone |
| 5,330,917 | A | 7/1994 | Stone |
| 5,364,792 | A | 11/1994 | Stone |
| 5,496,736 | A | 3/1996 | Stone |
| 5,514,593 | A | 5/1996 | Townsend et al. |
| 5,550,061 | A | 8/1996 | Stone |
| 5,567,619 | A | 10/1996 | Stone |
| 5,912,180 | A | 6/1999 | Stone |
| 6,248,593 | B1 | 6/2001 | Esswein et al. |
| 6,489,170 | B1 | 12/2002 | Cole |
| 6,800,485 | B2 | 10/2004 | Cole |
| 7,309,418 | B2 | 12/2007 | Joyce et al. |
| 7,604,997 | B2 | 10/2009 | Esswein et al. |
| 7,749,765 | B2 | 7/2010 | Demas et al. |
| 7,816,142 | B1 | 10/2010 | Frasca |
| 8,183,049 | B2 | 5/2012 | Kayano et al. |
| 9,213,022 | B1 | 12/2015 | Cullen |
| 9,823,188 | B1 | 11/2017 | Ram et al. |
| 2002/0187558 | A1 | 12/2002 | Bodkin et al. |
| 2008/0241943 | A1 | 10/2008 | Janda et al. |
| 2009/0208051 | A1 | 8/2009 | Emo et al. |
| 2011/0092377 | A1 | 4/2011 | Agrawal et al. |
| 2011/0283785 | A1 | 11/2011 | Askin et al. |
| 2013/0052741 | A1 | 2/2013 | Gozum |
| 2014/0287520 | A1 | 9/2014 | Ghodousi et al. |
| 2015/0212059 | A1 | 7/2015 | Schechter et al. |

FOREIGN PATENT DOCUMENTS

| | | |
|---|---|---|
| CA | 2893422 A1 | 12/2015 |
| CN | 102478526 B | 3/2014 |
| GB | 2235289 A | 2/1991 |
| JP | 2010127780 A | 6/2010 |
| JP | 2010271141 A | 12/2010 |
| WO | 9802224 A1 | 1/1998 |

OTHER PUBLICATIONS

Feigl, F. et al. "Analytical Use of Sodium Rhodizonate," Ind. Eng. Chem. Anal. Ed. 1942, 14, 10, 840-842. (Year: 1942).*
Jungreis, E. et al. "A simple direct estimation of ultramicroquantities of lead in drinking water using sodium rhodizonate," Microchemical Journal 34, 2, 1986, 219-221 (Year: 1986).*
Feng, L. et al. "Colorimetric filtrations of metal chelate precipitations for the quantitative determination of nickel(II) and lead(II)," Analyst, 2011, 136, 4197-4203 and ESI (Year: 2011).*
Bartsch, M.R. et al. "An Update on the Use of the Sodium Rhodizonate Test for the Detection of Lead Originating from Firearm Discharges," Journal of Forensic Sciences vol. 41 Issue: 6; DOI: 10.1520/JFS14047J; Abstract Only (Year: 1996).*
Feigl, Fritz and Anger, Vinzenz. Spot Tests in Inorganic Analysis. Sixth Edition. Translated by Ralph E. Oesper, Elsevier, 1972; pp. 282-287. (Year: 1972).*
Bartsch, M.R. et al. "An Update on the Use of the Sodium Rhodizonate Test for the Detection of Lead Originating from Firearm Discharges," Journal of Forensic Sciences vol. 41 Issue: 6; pp. 1046-1051 (Year: 1996).*
Feigl, F. et al. "Trace Detection by Means of Spot Reaction: I.-Detection of Traces of Lead in Water and Fine Chemicals," Analyst, 1944, 69, 147-149. (Year: 1944).*
Satarpai, T. et al. "Paper-based analytical device for sampling, on-site preconcentration and detection of ppb lead in water," Talanta 154 (2016) 504-510 (Year: 2016).*
(Hill, William et al.) Co-pending Application No. PCT/US19/46894 filed Aug. 16, 2019, Specification, Claims, Figures.
Abadin H, Ashizawa A, Stevens YW, et al. Toxicological Profile for Lead. Atlanta (GA): Agency for Toxic Substances and Disease Registry (US); Aug. 2007. 3, Health Effects).
Ashley, K. et al. Sampling and analysis considerations for the determination of hexavalent chromium in workplace air J. Environ. Monit., 2003, 5, 707-716.
ASTM D3559-15, Standard Test Methods for Lead in Water, ASTM International, West Conshohocken, PA, 2015, www.astm.org.
Bellinger DC, Very low lead exposures and children's neurodevelopment, Curr Opin Pediatr. Apr. 2008;20(2):172-7.
Co-pending Application No. PCT/US19/46894 International Search Report and Written Opinion, dated Dec. 4, 2019, 18 pgs.
International Patent Application No. PCT/US2019/046894, Invitation to Pay Fees dated Sep. 30, 2019, 2 pgs.
K.J. Pieper et al. Flint Water Crisis Caused by Interrupted Corrosion Control: Investigating "Ground Zero" Home Environ. Sci. Technol., 2017, 51 (4), pp. 2007-2014.
McCain et al. Field Screening For Hexavalent Chromium in Soil-A Fast-Turnaround Field Method Based on Water Extraction, Presented at Second International Conference: On-Site Analysis, Field Portable Instrumentation, Houston Texas, Jan. 24, 1994.
MQuant Lead Test, EMD Millipore Corporation, Aug. 2012(http://www.emdmillipore.com/us/en/product/Lead-Test,MDA_CHEM-110077).
T.R. Dulski, "A Manual for the Chemical Analysis of Metals", ASTM Manual Series: MNL 25, American Society for Testing and Materials, West Conshohocken, PA, 1996, 260 pgs.
Vitor H. M. Luiz et al., Rapid Determination of Lead in Progressive Hair Dye Lotion by Spot Test/Diffuse Reflectance Spectroscopy with a Paper Platform, J. Braz. Chem. Soc. vol. 26 No. 10 São Paulo Oct. 2015. http://dx.doi.org/10.5935/0103-5053.20150200.

* cited by examiner

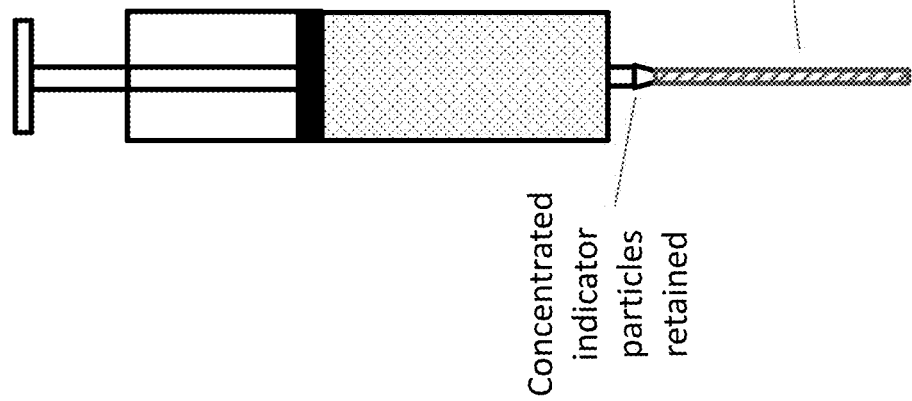
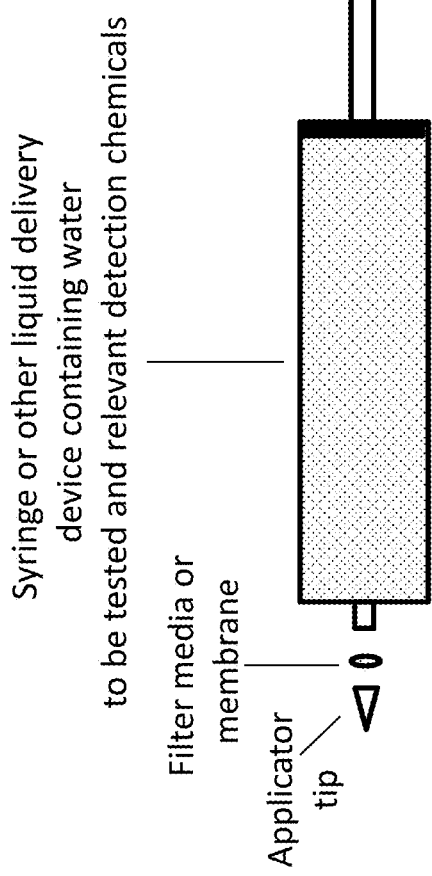
FIG. 1B
FIG. 1A

METHODS FOR DETECTION OF LEAD IN WATER

CROSS-REFERENCE TO RELATED APPLICATIONS

This application relies on the disclosure of and claims priority to and the benefit of the filing date of U.S. Provisional Application No. 62/719,454 filed Aug. 17, 2018, the disclosure of which is hereby incorporated by reference in its entirety.

STATEMENT OF GOVERNMENT INTEREST

This invention was made with government support under Contract # EP-D-17-042 awarded by the Environmental Protection Agency. The government has certain rights in the invention.

BACKGROUND OF THE INVENTION

Field of the Invention

The present invention generally relates to detection of substances in water such as lead. More particularly, embodiments of the invention provide methods, apparatuses, and kits for detection and analysis of such substances by forming a complex with an indicator reagent and filtering the complex on a filter or membrane. The concentrated indicator on the filter or membrane provides a colorimetric readout that can determine the amount of substance present in a water sample. Embodiments also provide computer-implemented methods for determining the concentration of a substance in a water sample based on the methods, apparatuses, and/or kits.

Description of Related Art

The toxic effects of lead exposure have been well-characterized both in human populations and animal models. In human populations exposed to lead, risks of health effects to cardiovascular, hematological, renal, endocrine, neurological, developmental, immunological, and reproductive systems have been observed (see Abadin H, Ashizawa A, Stevens Y W, et al. Toxicological Profile for Lead. Atlanta (Ga.): Agency for Toxic Substances and Disease Registry (US); 2007 Aug. 3, Health Effects). Children are particularly susceptible to the neurodevelopmental effects of lead exposure, and as one author concluded, "no level of lead exposure appears to be 'safe' and even the current 'low' levels of exposure in children are associated with neurodevelopmental deficits" (see Bellinger D C, Very low lead exposures and children's neurodevelopment, Curr Opin Pediatr. 2008 April; 20(2):172-7).

The recent water crisis in Flint, Michigan underscores the threat of exposure to lead in potable water from plumbing materials. In that case, the city switched to the Flint River as a temporary drinking water source without implementing corrosion control, which resulted in lead concentrations in water samples from Flint residences well-exceeding the recommended levels for lead in drinking water (see K. J. Pieper et al. Flint Water Crisis Caused By Interrupted Corrosion Control: Investigating "Ground Zero" Home Environ. Sci. Technol., 2017, 51 (4), pp 2007-2014). The existing regulation controlling waterborne lead exposure is the U.S. Environmental Protection Agency (EPA) Lead and Copper Rule (LCR), which provides a lead action level of 15 µg/L. According to the LCR, if lead concentrations exceed an action level of 15 ppb in more than 10% of customer taps sampled, the water treatment system must undertake a number of additional actions to control corrosion (see 40 CFR Part 141 Subpart I).

Standard test methods for assessing lead concentration in water include atomic-absorption spectrophotometry and differential pulse anodic stripping voltammetry (see ASTM D3559-15, Standard Test Methods for Lead in Water, ASTM International, West Conshohocken, PA, 2015, www.astm.org). However, these require highly expensive, specialized equipment that can only be used in a laboratory by trained scientists or technicians. There is a pressing need for a reliable means for testing water samples for lead or other toxic substances that can be used by anyone anywhere, including laypeople concerned about such contamination in their drinking water.

SUMMARY OF THE INVENTION

Embodiments of the invention provide a method and apparatus for detecting a material of interest (whether soluble and/or insoluble) in water. According to embodiments, the material is detected by first forming a complex with one or more indicator reagents, then inducing precipitation of the complex which is then filtered and accumulated on a membrane.

By accumulating the complex on the membrane, the indicator is concentrated so that indicator molecules can be visually detected. The amount of indicator particles observed on the membrane is positively correlated with the concentration of the material of interest. The concentration of the material or substance of interest that can be detected in a sample can range from above 0 ppb to 100%, whether the substance of interest is present in the sample in soluble form, or insoluble form, or both soluble and insoluble forms. Detection ranges for the substance of interest in the sample can range from 0.01 ppb to 500 ppb, or from 0.05 ppb to 1 ppm, or from 0.1 ppb to 10 ppm, or from 0.5 ppb to 50 ppm, or from 1 ppb to 15 ppb, or from above 0 ppb to 5 ppb, or from 2 ppb to 20 ppb, or from 10 ppb to 100 ppm, or from 50 ppb to 1,000 ppm, or from 500 ppm to 10%, or from 750 ppm to 50%, or from 1% to 25%, or from 5% to 80%, or any ranges in between, including any ranges with any of these endpoints.

According to other embodiments, a separate "developer" solution is used to enhance the color contrast of the indicator particles through induction of a morphological change in the complex or indicator such as crystallization, rather than formation of a different reactant.

According to embodiments, the visual presence of the indicator serves as a means of yes/no detection (i.e. a screening device). Alternatively or in addition, the accumulation of indicator particles and their resulting color intensity can be compared to calibrated standards to approximate the concentration of the material of interest.

According to embodiments, a testing apparatus is provided which is capable of hosting a reaction in which a complex is formed with a material of interest and an indicator reagent. The apparatus can include a pump, syringe, tubing, hosing or other device/apparatus capable of holding or transferring water or other matrix (such as a syringe, pump, tubing or hosing or a syringe or pump with tubing or hosing) which may contain a material of interest, and a filter or membrane which is configured to fit at the end of the device/apparatus. When a soluble indicator reagent is added to the water sample inside the device/apparatus, the resulting complex which is formed with the material of interest can be subsequently forced through the filter at the end of the device/apparatus, thereby capturing and concentrating the indicator on the filter. Other means of concentrating and recovering particles from water can also be used, including but not limited to evaporation, distillation, centrifugation, precipitation, electrostatic/ionic/magnetic/charged retention and combinations thereof, for example.

According to other embodiments, a kit is provided which encompasses the above test apparatus and one or more indicator reagents. The kit can also include a set of instructions for carrying out the methods of the invention by way of the test apparatus and one or more indicator reagents.

According to other embodiments, the method, apparatus, and/or kit can be integrated with a mobile phone or other portable computing device with a camera and display, which together can enable automated reading of material concentration as well as allow for reporting of geotagged data to map test results gathered across an area.

While one particular embodiment demonstrated in this disclosure is used to detect lead in water, it is contemplated that the methods and apparatus described herein can be modified to detect any material that is capable of forming a filterable or recoverable complex with a water-soluble indicator. These embodiments and additional embodiments will be set forth in the foregoing Detailed Description.

BRIEF DESCRIPTION OF THE DRAWINGS

The accompanying drawings illustrate certain aspects of embodiments of the present invention and should not be used to limit the invention. Together with the written description the drawings serve to explain certain principles of the invention.

FIGS. 1A and 1B are renderings showing a prototype of an apparatus according to an embodiment of the invention.

DETAILED DESCRIPTION OF VARIOUS EMBODIMENTS OF THE INVENTION

Figure 2A:
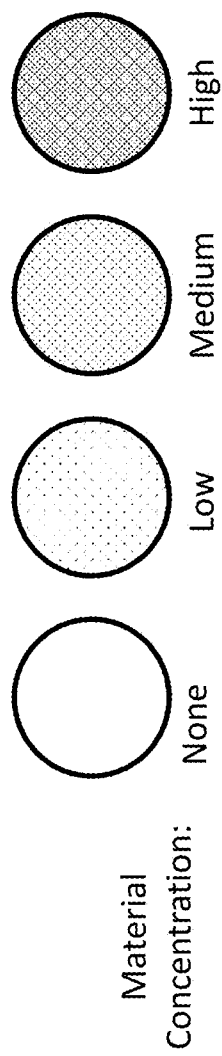
FIG. 2A is a rendering of visual indication of lead concentration in water samples via membrane retention of lead rhodizonate indicator according to an embodiment of the invention and FIGS. 2B and 2C are graphs showing the corresponding correlation of lead concentration to color intensity as measured in the laboratory.

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

According to embodiments of the methods, apparatuses, and kits described herein, a water-soluble reagent is added to a water sample to react with the chemical requiring detection (whether said chemical is in soluble and/or in particulate form) to form an insoluble precipitate inside a testing device/apparatus holding the water sample (which may be a pump, syringe, tubing, or other item capable of holding or transporting fluid). According to embodiments, the water-soluble reagent can be added to the water sample at a concentration which is in stoichiometric excess of the suspected amount of the chemical requiring detection such that the reagent binds with all instances of soluble or insoluble forms of the chemical in the water sample to form a colored precipitate.

A filter membrane or other suitable capture device is attached to the end of the apparatus which catches the formed indicator precipitates, which accumulate as the solution is forced out of the apparatus and through the membrane. Other capture devices can include evaporation, distillation, centrifugation, precipitation and/or electrostatic/ionic/magnetic/charged retention devices or any method or device which relies on one or more of these separation techniques, or similar separation techniques, or any separation technique now or later made available. An embodiment of an apparatus with its individual components is shown in FIG. 1A. The figure shows (from right to left), a syringe, a filter, and an end portion that can fit at the end of the syringe and hold the filter. FIG. 1B shows the assembled apparatus during use. The accumulation of these indicator precipitates enables visual indication of the chemical to be detected which can also be correlated to the concentration of the chemical to be detected. A separate developer solution can be added to the water sample inside the testing apparatus or to the membrane with the particulates in order to induce a brighter coloration in the indicator precipitates or to improve specificity (i.e. ensure any coloration is a result of the compound intended for detection and not an interferent).

The methods, apparatuses, and kits differ from chromatographic assays currently on the market, which typically rely on all components being soluble or dispersible, where the solution itself is measured for color intensity to indicate the presence of a chemical. According to embodiments, the indicator particles themselves are precipitated and captured (i.e. the reaction responsible for detection occurs while in solution) which advantageously reduces the steps required in comparison to prior art methods and dramatically improves the ability for a layman customer to use the methods, apparatuses, and kits for at-home testing.

According to the embodiment demonstrated herein, sodium rhodizonate (CAS No. 523-21-7) is used as the reagent to detect lead, and tartaric acid is used as a developer.

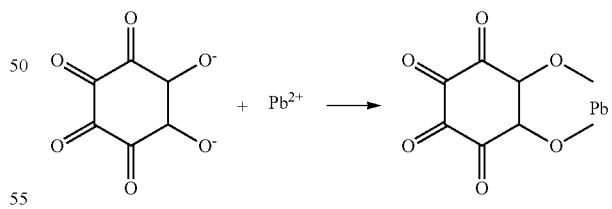

As shown in the reaction scheme above, an aqueous solution of sodium rhodizonate produces colored precipitates from neutral or slightly acidic lead solutions (see Vitor H. M. Luiz et al., Rapid Determination of Lead in Progressive Hair Dye Lotion by Spot Test/Diffuse Reflectance Spectroscopy with a Paper Platform, J. Braz. Chem. Soc. vol. 26 no. 10 São Paulo October 2015. http://dx.doi.org/10.5935/0103-5053.20150200). The sodium rhodizonate reagent is water soluble, forming a yellow/orange solution, while the sodium rhodizonate-lead adduct forms a pink/red precipitate, where the color is developed (for example using a developer such as tartaric acid) through crystallization of the lead rhodizonate particles which form a duller amorphous morphology by default. Other rhodizonate compounds have also been demonstrated as reagents for lead detection including potassium rhodizonate, barium rhodizonate, and strontium rhodizonate. However, the present inventors have discovered that the rhodizonate reagent can form complexes with both soluble and insoluble lead present in water. As an embodiment, a dilute base, including but not limited to sodium hydroxide or potassium hydroxide, can be added neutralize the developer, thereby preserving the precipitate indefinitely.

In one verified configuration, a sample to be tested (such as water) is added to a reaction container (such as a device/apparatus for example a syringe) along with a water-soluble indicator reagent capable of indicating the presence of a substance of interest (such as a rhodizonate compound like sodium rhodizonate, which can be in powder, tablet, or capsule form). The reagent can be added to the water sample at a concentration in the range of above 0 M to 1M or more, such as from above 0 to 1 uM, to 10 μM, to 100 μM, to 250 μM, to 500 μM, to 1 mM, to 2 mM, to 5 mM or more. Further for example the reagent can be present in the water sample at a concentration in the range of from 1 μM to 500 μM, or from 50 μM to 250 μM, or from 750 μM to 1.5 mM, or from 1 mM to 3 mM, or from 5 mM to 10 mM, or from 500 μM to 100 mM, or from 1 mM to 500 mM, or from 250 mM to 1 M, or from 500 mM to 1 M, or any combinations of the endpoints of these ranges or any range in between these ranges, such as from 1 μM-1M. The sodium rhodizonate reacts almost instantly with any lead present in the water, whether in the form of soluble lead compounds such as lead carbonate and lead acetate or insoluble particles including elemental lead and lead chromate. A filter membrane or paper, or other capture device is attached to the end of the syringe and then the test water is forced through the membrane by depressing the syringe. Other capture devices can include evaporation, distillation, centrifugation, precipitation and/or electrostatic/ionic/magnetic/charged retention devices or any method or device which relies on one or more of these separation techniques, or similar separation techniques, or any separation technique now or later made available. The amorphous lead rhodizonate particulates which have formed are then captured on the membrane and concentrated as the water is expelled. The present inventors have found that addition of a developer, such as tartaric acid, either in liquid form upon the membrane after water is expelled or by insertion into the syringe/tubing along with the reagent in tablet or capsule form, induces crystallization of the lead rhodizonate precipitates which appear as a vibrant pink-scarlet color that is highly visible to the naked eye. The retention of indicator precipitates using a standard test volume of water allows for semi-quantitative estimation of lead concentration, as the color intensity increases with increased lead content. The standard test volume of the water sample can be any quantity of test sample such as above 0 ml to 500 ml or more, but is preferably in the range of 5 ml to 250 ml or 300 ml, or according to any standard device/apparatus (such as a syringe) volume. In an exemplary embodiment, 5 mg of sodium rhodizonate (in powder form, in a capsule, in solution, or in a tablet with binders such as ethylene oxide) is added to 100 mL of water inside a syringe. Insoluble lead rhodizonate precipitates fall out of solution and are captured on a membrane attached to the tip of the syringe as it is depressed. One drop of 10% w/v tartaric acid added to the membrane is sufficient to convert the captured amorphous lead rhodizonate precipitates to their more vividly-colored crystalline form. The visual limit of detection for lead using 100 mL of water and a membrane diameter of 4 mm has been shown to be less than 5 ppb Pb.

In a second demonstrated embodiment, a hose is directly attached to the water source (i.e. spigot or faucet) and slow-release tablets of reagent and developer are contained within the hose (such as via in-line strainer baskets, though the developer may instead be added in droplet form afterwards to the membrane). A filter membrane is attached to the end of the hose, and the water source is released, allowing flow of water until a set volume has passed (as measured by flowmeter or by simply measuring the volume in a marked container). This embodiment allows for a greater volume of water to be tested than the syringe method, which can enhance resolution and lower detection limits since more lead rhodizonate indicator can accumulate on the test membrane. In this embodiment, detection of lead at concentrations as low as 2 ppb in 500 mL of water has been demonstrated using 50 mg of sodium rhodizonate and the same 10% w/v tartaric acid developer added in droplet form to the membrane. It logically follows that evaluation of larger volumes of water (or use of a membrane of smaller diameter, though this reduces flow rates) will further reduce the lowest detectible concentration.

Figure 2B:
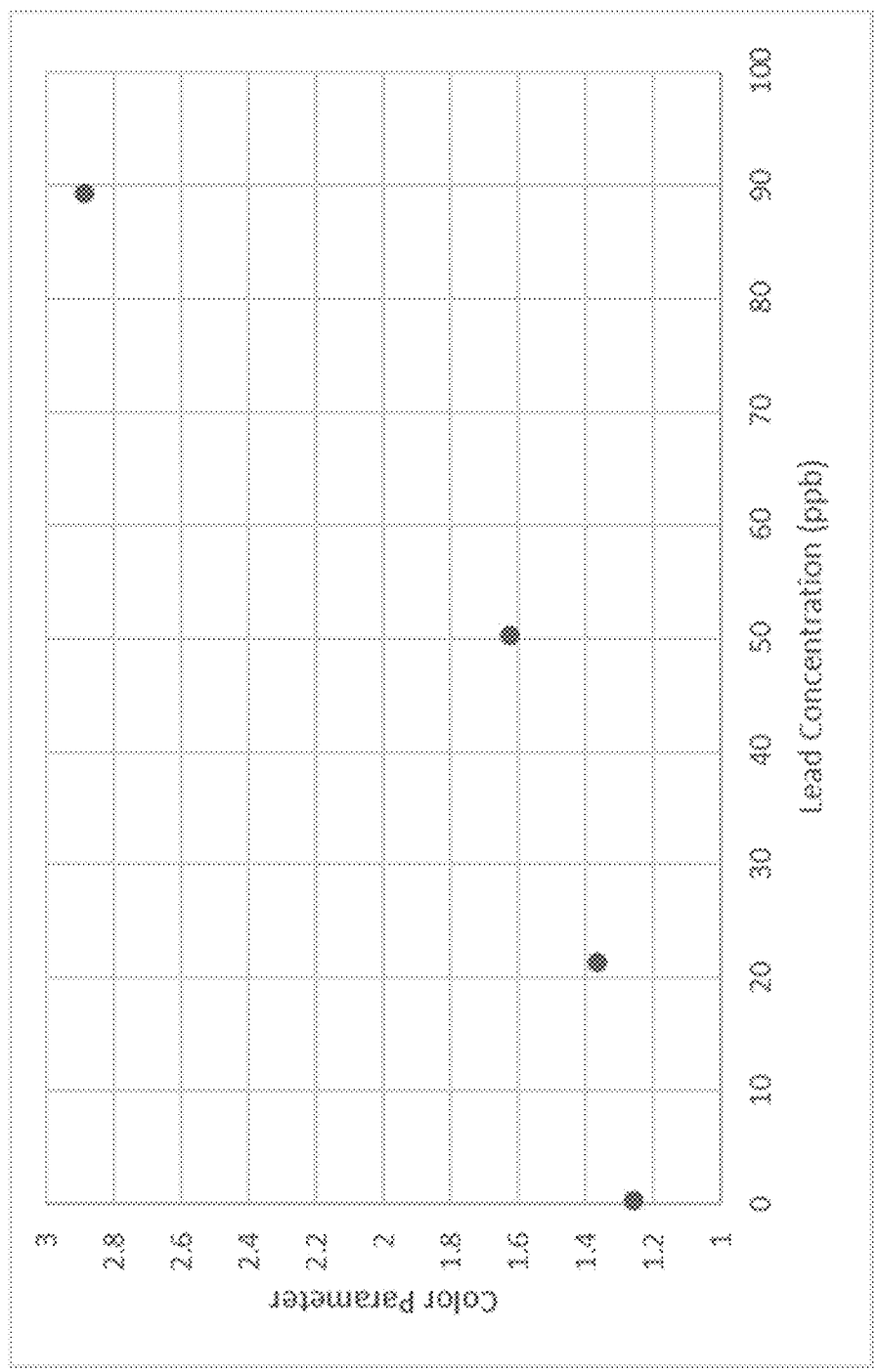
Figure 2C:
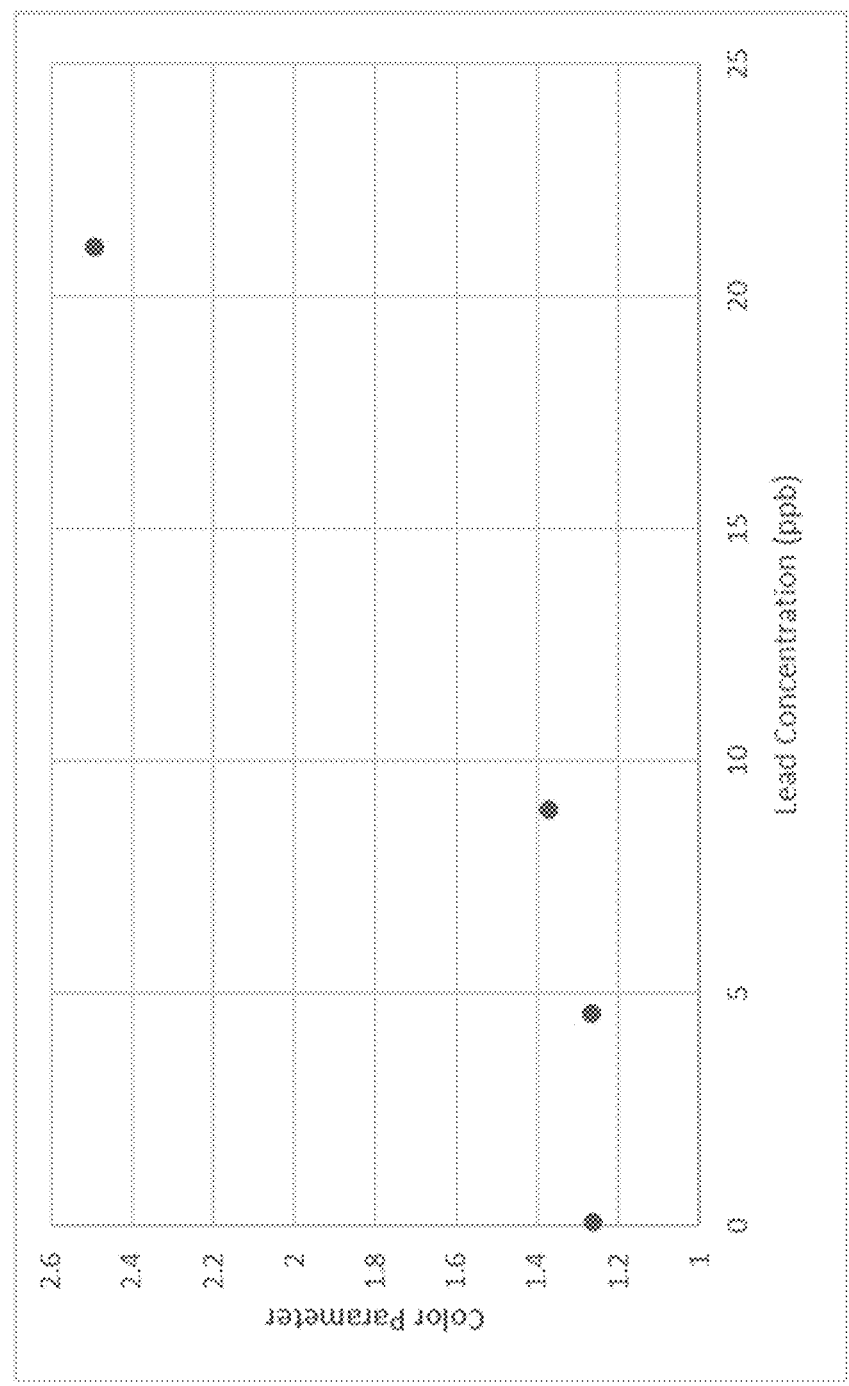

FIG. 2 shows visual indication of lead via membrane retention of lead rhodizonate indicator. As shown in the figure, the amount of lead in standard solutions is positively correlated with the intensity of coloration accumulated on the filter. Thus, by comparing the amount of coloration resulting from a test sample from that of known standards, the amount of lead in the test sample can be determined semi-quantitatively. The demonstrated embodiment takes advantage of the accumulating indicator precipitate to relate the color to the lead concentration. Further, such semi-quantitative detection can be advantageously made more convenient for an end user by the use of printed calibrated color standards, obviating the need to for the end user to run standards. For example, calibrated color standards printed on a card to which the test substrate can be attached enable the user to approximate their lead concentration. In embodiments, the card can be cardboard, paper, plastic, metal, glass or other suitable substrate material.

Figure 3A:
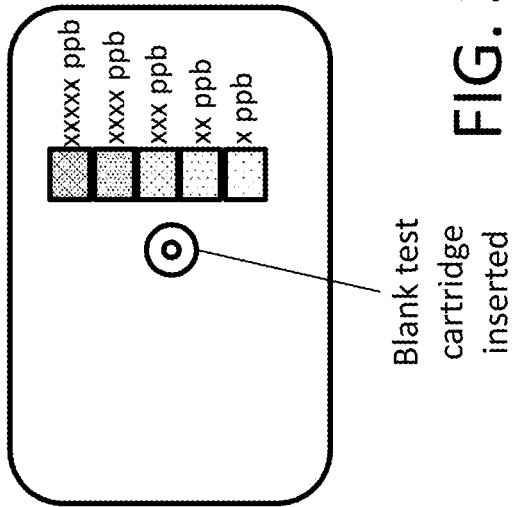
FIGS. 3A-3C are renderings showing components of a kit for semi-quantitative detection of lead according to an embodiment of the invention.
Figure 3B:
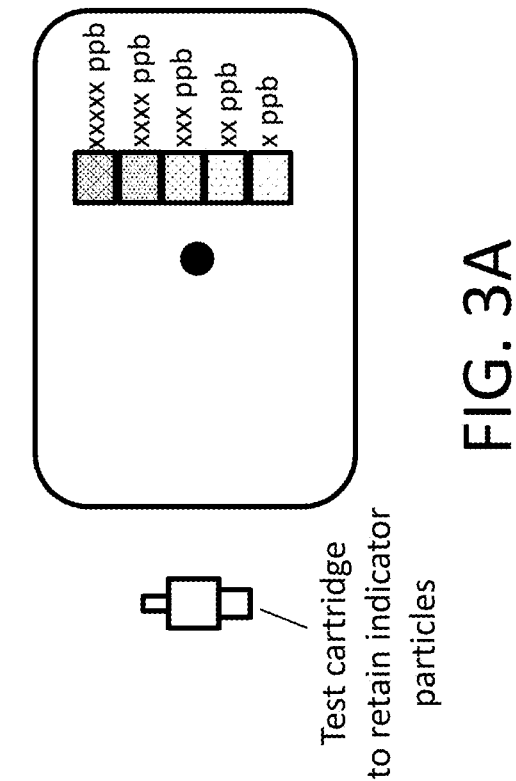
Figure 3C:
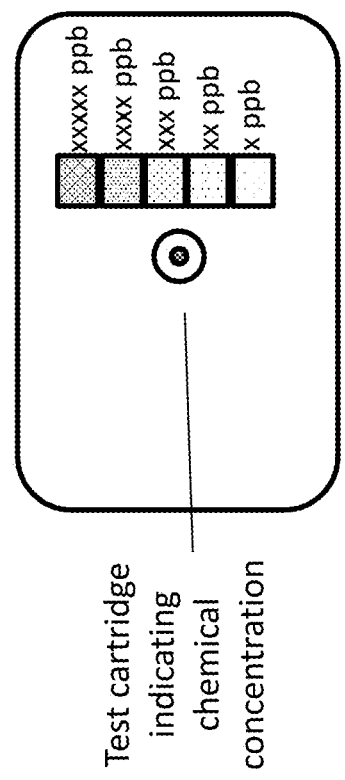

Such semi-quantitative measuring of lead from a test sample is shown in the embodiment depicted in FIGS. 3A-3C, which depict a calibrated color chart. FIG. 3A shows such embodiment with its removable test insert, as assembled in FIG. 3B. FIG. 3C shows detection of lead with concentration corresponding to the adjacent calibrated color chart. Lead concentrations as low as 4.5 ppb have been repeatably detected using this prototype, and with optimization detecting even lower concentrations is possible (2 ppb has been detected, but further refinements are required to maintain repeatability).

According to embodiments, such printed calibrated color standards are included as part of a kit for determining lead concentrations, for example by using calibrated color standards capable of visual matching of a colored precipitate to a color representing a known concentration of the substance of interest, wherein the visual matching can involve visual matching of a colored precipitate (including the infrared through visible and ultraviolet light spectrum). The kit can include 1. a syringe device with a filter (such as depicted in FIGS. 1A and 1B) or tubing with such a filter 2. a predetermined amount of rhodizonate reagent (e.g. in powder, tablet, or capsule form) 3. printed calibrated color standards (such as depicted in FIGS. 3A-3C) and 4. a set of printed instructions for carrying out the methods of the invention.

The kit can also include a developer to be added to the water sample or the filtered precipitate for inducing a morphological change (such as crystallization) in the colored precipitate on the filter during use of the kit. The printed instructions can include written text and diagrams for using the syringe device with filter, rhodizonate reagent, developer, and printed calibrate color standards for determining lead concentration in water. Use of other reagents to detect different substances would use similar methods and a similar reagent concentration range; in most cases, above 0 and up to 1 M of reagent, such as 1 µM-1M of reagent, will be sufficient (such as barium chloride as a reagent for the detection of sulfates or diphenylcarbohydrazide for the detection of hexavalent chromium) (see other pairings of reagents and substances of interest in the chart below which can be used in the kits of the invention). An additional embodiment may use consumer products (such as single-serving type pod-based coffee makers) with the chemical detection compounds located inside the product. In this exemplary embodiment, a single serving coffee pod (e.g., K-cup brand coffee pods) contains the reagent and developer, which are inserted into the coffeemaker and "brewed". The reacted precipitates could be collected in the mug or other container below using gravimetric filtration or similar means, or reagent precipitates could be collected on a filter disposed in or on the coffee pod at a position where the water/substrate would exit the coffee pod after having contacted the reagent and optionally the developer during the "brewing" process.

Figure 4:
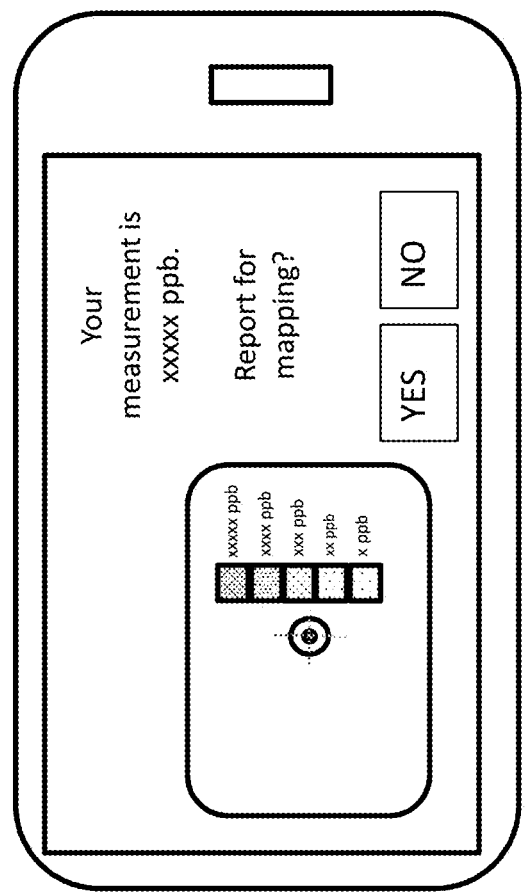
FIG. 4 is a rendering showing a graphical user interface of a mobile application for automated reading and reporting of lead concentration according to an embodiment of the invention.
Figure 4:
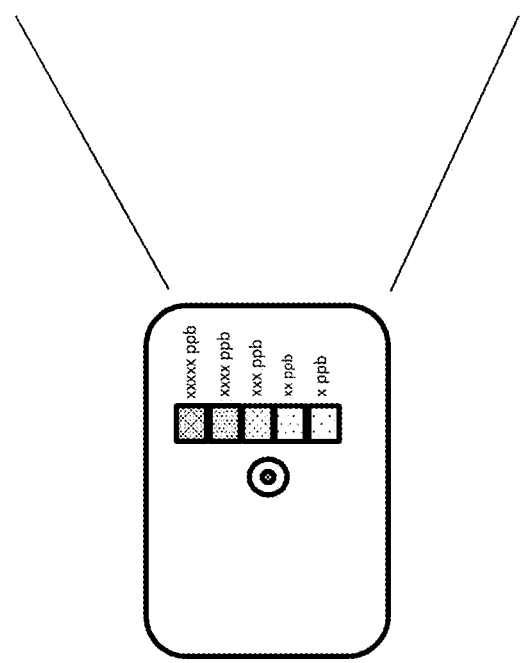

Complementary to these embodiments, a mobile application or computer-implemented method for a portable computing device can enable automated reading of lead concentration as well as geotag and report the data to a central database where the collective crowdsourced data could be used to indicate the initiation of a lead crisis as well as help map the scope and severity of the issue to expedite remediation. FIG. 4 shows a graphical user interface for such mobile application. The user interface allows capture of the resulting colored indicator by way of the built in camera of a mobile phone, smart phone, tablet, laptop, or similar portable computing device. As shown in FIG. 4, a guide appears on the camera display as well as instructions for aligning the circle with the filter with colored indicator. In this way, color data from the filter can be captured by way of the built in camera. According to embodiments, the mobile application includes algorithms for determining the lead concentration based on the intensity of captured color of the indicator or other color data, a reporting feature for communicating the determined lead concentration with a central database, and a geotagging feature which determines the geographical coordinates of the phone by way of GPS, or allows a user to enter coordinates or the residence of the water source which was tested.

By way of example only, the mobile application can quantify the captured colorimetric readout taken by the camera of the mobile phone or other portable device. The mobile application can allow quantification of various color data of the captured colorimetric readout such as hue, saturation, lightness, and temperature. Alternatively or in addition, the mobile application can work with various external instruments for measuring such color data such as a professional color meter or color analyzer. According to embodiments, the mobile application allows a user to store a standard curve of color data from colorimetric readouts based on samples of known lead concentrations. The mobile application can then calculate the concentration of lead of an unknown sample based on the stored standard curve. In addition or alternatively, the mobile application can allow a user to semi-quantitatively estimate the lead concentration by comparison to color standards stored and displayed in the mobile application. The user can compare the captured color readout to the displayed color standards and thus estimate the concentration range of the sample.

The mobile application can be implemented in computer-readable code, computer-readable instructions, computer-executable instructions, or "software". The computer-readable instructions can be programmed in any suitable programming language, including JavaScript, C, C#, C++, Java, Python, Perl, Ruby, Swift, Visual Basic, and Objective C. By such programming the computer-readable instructions, code, or software instruct a processor of the portable computing device to carry out the operations and commands of the mobile application. The color data captured by the portable computing device or external color meter and the computer-executable instructions can be stored in the portable computing device's memory. The memory can be a non-transitory computer storage media such as RAM. As used in the context of this specification, a "non-transitory computer-readable medium (or media)" may include any kind of computer memory, including magnetic storage media, optical storage media, nonvolatile memory storage media, and volatile memory. Non-limiting examples of non-transitory computer-readable storage media include floppy disks, magnetic tape, conventional hard disks, CD-ROM, DVD-ROM, BLU-RAY, Flash ROM, memory cards, optical drives, solid state drives, flash drives, erasable programmable read only memory (EPROM), electrically erasable programmable read-only memory (EEPROM), non-volatile ROM, and RAM.

Additional embodiments of the invention include a computer system for carrying out the computer-implemented methods of the invention. The computer system can include a processor for executing the computer-executable instructions, one or more databases described herein, a user interface, and a set of instructions (e.g. software) for carrying out the method. The computer system can include a stand-alone computer, such as a desktop computer, a portable computer, such as a tablet, laptop, PDA, or smartphone, or a set of computers connected through a network including a client-server configuration and one or more database servers. The network can use any suitable network protocol, including IP, UDP, or ICMP, and may be any suitable wired or wireless network including any local area network, wide area network, Internet network, telecommunications network, Wi-Fi enabled network, or Bluetooth enabled network.

In one embodiment, the computer system includes a central computer connected to the Internet that has an internal database capable of storing data reported from remote portable computing devices such as lead concentration, time and date of measurement, and geographical or residential location of measurement. The database can be a standard relational database that communicates by way of a database server with the portable computing devices loaded with the mobile application in the memory of the portable computing devices. The central computer can include a set of computer-executable instructions stored in memory which can be used to monitor lead concentrations reported from the portable computing devices. By way of further example, the computer-executable instructions on the central computer can allow a user to set a concentration threshold that triggers an alarm, text message, or other suitable notification to a user. The computer-executable instructions can also allow for visual monitoring of lead concentrations reported in an area by way of a heat map or other suitable graphical format for display on the central computer's screen or graphical display, or allow for monitoring by display on a remote computing device. Such central computer can be used for monitoring lead concentrations in water samples such as tap water by personnel of a health agency, water utility, and/or regulatory authority.

While detection of lead via the above methods has been most thoroughly demonstrated, detection of other materials is also possible by the same mechanism (i.e. inducing colored particulate indicator formation in situ for membrane capture). The table below indicates a few examples for illustrative sake; it is not nearly comprehensive nor inclusive of all possibilities. Any metal (soluble or insoluble), anion, or cation that forms a colored precipitate with a water-soluble reagent can be detected.

TABLE I

Examples of Detection of Other Materials

| Material to Detect | Reagent | Indication |
| --- | --- | --- |
| Aluminum | Eriochrome cyanine | Green/yellow |
| Cadmium | 1-(2-Pyridylazo)-2-naphthol (PAN) | Green to red |
| Cobalt | 1-(2-Pyridylazo)-2-naphthol (PAN) | Green to red |
| Chromium | Diphenylcarbohydrazide | Red/violet |
| Copper | Bicinchoninic acid | Purple |
| Cyanide | Pyridine-Barbituric Acid | Red/violet |
| Fluoride | SPADNS method | Red to colorless |
| Iron | Bipyridyl or 1,10-phenanthroline | Reddish purple |
| Mercury | TMK | Red/purple |
| Nickel | Dimethylglyoxime | Red |
| Palladium | Dimethylglyoxime | Yellow |
| Phosphorus | Molybdoranadate | Yellow |
| Potassium | Tetraphenylboron | White |
| Sulfate | Barium Chloride | White |

Additional examples of colored precipitate indicator formation can be found in the scientific literature (for example, see T. R. Dulski, "A Manual for the Chemical Analysis of Metals", ASTM Manual Series: MNL 25, American Society for Testing and Materials, West Conshohocken, PA, 1996, incorporated by reference in its entirety). Other examples and general principles can be found in analytical chemistry textbooks (for example, see Chemistry with Inorganic Qualitative Analysis, Third Edition; Therald Moeller, John C. Bailar, Jr., Jacob Kieinberg, Cyrus O. Guss, Mary E. Castellion, and Clyde Metz. Harcourt Brace Jovanovich: New York. NY, 1989; and Chemistry: Inorganic Qualitative Analysis in the Laboratory. Metz, C., Castellion, Mary E. 1989. Academic Press, Inc.: New York, NY, 1980, each incorporated by reference in their entireties).

For example, any of the above reagents would be substituted for rhodizonate indicator and used to detect the contaminant of interest. Further for example in an embodiment the reagent diphenylcarbohydrazide would be substituted for rhodizonate to detect chromium (i.e. hexavalent chromium, Cr6+) by way of a red/violet complex as shown in the reaction scheme below:

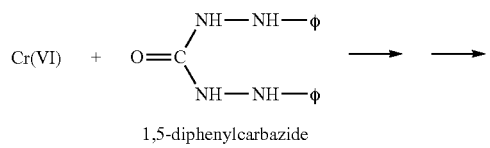

1,5-diphenylcarbazide

-continued

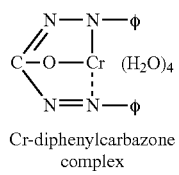

Cr-diphenylcarbazone complex (from K. Ashley et al., "Sampling and analysis considerations for the determination of hexavalent chromium in workplace air" J. Environ. Monit., 2003, 5, 707-716).

The complex can be filtered according to the apparatuses, methods, and kits described herein and accumulate on a membrane where it can be measured semi-quantitatively or quantitatively as described above for lead. Similarly, the present invention contemplates substitution of any of the above reagents for detection of the materials in the left column of Table I, or any other reagent known to form a filterable, colored precipitate with a target compound. As such, the present invention provides apparatuses, methods, and kits for detecting any target compound in water that can form a filterable, colored complex with a water-soluble indicator reagent.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A method for detection of lead in water, comprising:
   i) obtaining a sample containing water to be tested;
   ii) adding a water-soluble reagent comprising rhodizonate to the sample, which reagent is capable of forming an initial colored precipitate with lead in the sample, if present;
   iii) passing the sample and the water-soluble reagent through a filter or a membrane, wherein the filter or the membrane is configured to retain the initial colored precipitate;

iv) after passing the sample and the water-soluble reagent through the filter or the membrane, adding an acidic developer to the filter or the membrane, wherein when lead is retained on the filter or the membrane the developer is capable of inducing formation of a subsequent colored precipitate;

v) observing color intensity of the subsequent colored precipitate, if any, on the filter or the membrane and determining a concentration of the lead in the sample by comparing the observed color intensity to a set of calibrated color standards.

2. The method of claim 1, wherein the rhodizonate is sodium rhodizonate, potassium rhodizonate, barium rhodizonate, or strontium rhodizonate, or combinations thereof.

3. The method of claim 1, wherein the developer is tartaric acid.

4. The method of claim 1, wherein the sample comprises soluble and/or insoluble lead.

5. The method of claim 4, wherein the water-soluble reagent comprising rhodizonate is added in a stoichiometric excess to the soluble and/or soluble lead in the sample.

6. The method of claim 1, wherein the sample comprises lead.

* * * * *